(12) United States Patent
Shin et al.

(10) Patent No.: US 9,631,280 B2
(45) Date of Patent: Apr. 25, 2017

(54) METHOD OF MANUFACTURING PALLADIUM THIN FILM BY USING ELECTROLESS-PLATING METHOD

(71) Applicant: SOONGSIL UNIVERSITY RESEARCH CONSORTIUM TECHNO-PARK, Seoul (KR)

(72) Inventors: Kuan Soo Shin, Seoul (KR); Young Kwan Cho, Incheon (KR)

(73) Assignee: SOONGSIL UNIVERSITY RESEARCH CONSORTIUM TECHNO-PARK, Seoul (KR)

(*) Notice: Subject to any disclaimer, the term of this patent is extended or adjusted under 35 U.S.C. 154(b) by 0 days.

(21) Appl. No.: 14/467,032

(22) Filed: Aug. 24, 2014

(65) Prior Publication Data

US 2015/0056378 A1 Feb. 26, 2015

(30) Foreign Application Priority Data

Aug. 23, 2013 (KR) .................. 10-2013-0100495

(51) Int. Cl.
| | |
|---|---|
| C23C 18/16 | (2006.01) |
| C23C 18/44 | (2006.01) |
| G01N 21/65 | (2006.01) |
| B82Y 15/00 | (2011.01) |
| C23C 18/18 | (2006.01) |
| C23C 18/20 | (2006.01) |

(52) U.S. Cl.
CPC .......... *C23C 18/44* (2013.01); *C23C 18/1676* (2013.01); *B82Y 15/00* (2013.01); *C23C 18/1893* (2013.01); *C23C 18/2086* (2013.01); *G01N 21/65* (2013.01)

(58) Field of Classification Search
CPC ....... C23C 18/19; C23C 18/1673; C23C 18/44
USPC ...................................................... 427/443.1
See application file for complete search history.

(56) References Cited

U.S. PATENT DOCUMENTS

| | | | | |
|---|---|---|---|---|
| 3,798,056 A | * | 3/1974 | Okinaka ............... | C23C 18/163 118/409 |
| 4,804,410 A | * | 2/1989 | Haga ...................... | C23C 18/44 106/1.15 |
| 5,925,415 A | * | 7/1999 | Fry ...................... | C23C 18/1658 427/304 |

(Continued)

FOREIGN PATENT DOCUMENTS

| | | |
|---|---|---|
| KR | 10-2003-0059743 A | 7/2003 |
| KR | 10-2006-0067453 A | 6/2006 |

*Primary Examiner* — David Turocy
(74) *Attorney, Agent, or Firm* — Revolution IP, PLLC

(57) ABSTRACT

Provided is a method of manufacturing a palladium (Pd) thin film by using an electroless-plating method, the method including: manufacturing a reaction mixture by adding Pd salt and an alkaline pH regulator to an alcohol-water mixed solution; and forming a Pd thin film by loading and stirring the reaction mixture in a substrate. Accordingly, a Pd thin film having a surface enhancement Raman scattering (SERS) effect may be easily manufactured without having to use expensive additional equipment, such as a vacuum device, and in detail, electroless-plating may be performed even on an insulating substrate formed of, for example, glass. In addition, since a size of the Pd thin film manufactured on the substrate may be adjusted, the Pd thin film may be applied to various electrochemical products.

2 Claims, 3 Drawing Sheets

(56) References Cited

U.S. PATENT DOCUMENTS

| | | | |
|---|---|---|---|
| 2007/0298190 A1* | 12/2007 | Kobori | ............... C03C 17/25 |
| | | | 427/595 |
| 2011/0236565 A1 | 9/2011 | Piano et al. | |
| 2013/0081540 A1 | 4/2013 | Lee et al. | |
| 2014/0072706 A1* | 3/2014 | Long | ............... C23C 18/1844 |
| | | | 427/125 |

* cited by examiner

METHOD OF MANUFACTURING PALLADIUM THIN FILM BY USING ELECTROLESS-PLATING METHOD

CROSS-REFERENCE TO RELATED PATENT APPLICATION

This application claims the benefit of Korean Patent Application No. 10-2013-0100495, filed on Aug. 23, 2013, in the Korean Intellectual Property Office, the disclosure of which is incorporated herein in its entirety by reference.

BACKGROUND OF THE INVENTION

1. Field of the Invention

The present invention relates to a method of manufacturing a palladium (Pd) thin film, and more particularly, to a method of manufacturing a Pd thin film having increased activity of surface enhanced Raman scattering (SERS) by using an electroless-plating method.

2. Description of the Related Art

Generally, a palladium (Pd) thin film is manufactured by using one of three methods, i.e., an electroplating or electro-deposition method, a vapor deposition method, and an electroless-plating method.

In the electro-deposition method, elaborate and expensive equipment is required to guarantee deposition at an accurate ratio and a suitable electric potential. Moreover, in the electro-deposition method, an electric contact should be performed on a plating surface. In addition, not only a long time is taken for such an electric contact if an integrated circuit (IC) having a very complex circuit pattern, specially a certain high density, is used, and also it is difficult to manufacture a thin film. Furthermore, a surface that is plated should be conductive, and should be connected to an external power source, such as a voltage source or a current source.

Also, even the vapor deposition method has a few intrinsic weaknesses. In various application fields, elaborate and high vacuum equipment is required, and a large amount of Pd metal is consumed during an evaporation process. However, it is difficult to attach evaporated Pd only to a selected area in a plated surface. In other words, it is not easy to design a pattern having Pd by using the vapor deposition method.

Meanwhile, effects of surface enhanced Raman scattering (SERS) may increase according to changes in a surface or structure of a metal. A technology using such SERS is applied to various fields, for example, chemical analysis, corrosion, lubrication, catalysis, sensor, and molecular electronics.

However, SERS shows a large effect when a noble metal, such as gold (Au), silver (Ag), or copper (Cu) is used, and such a limitation hinders SERS from being variously used.

However, it is recently proven that SERS is active even in a transition metal if roughening is suitably adjusted. However, it is difficult to obtain a Raman spectrum of molecules under a non-electrochemical environment, in detail, in a transition metal, such as platinum (Pt) or Pd.

Accordingly, KR 10-2004-0106238 discloses an Ag electroplating method using Pt-Ag activation method. Here, a core without a seed layer is generated on a substrate having a high specific resistance during a semiconductor metal wire process such that electroplating is possible via an activation method, and then Ag electroplating is performed to form a uniform Ag thin film without a defect such that Ag having a low specific resistance is used as a material for a highly integrated semiconductor wire process.

Although a general electroplating method discloses an electric gilding method using Pd, but a thin fill is still formed by using electricity, and the thin film cannot be formed on an insulating substrate.

SUMMARY OF THE INVENTION

The present invention provides a method of manufacturing a palladium (Pd) thin film easily having an activity effect of surface enhancement Raman scattering (SERS) by using an electroless-plating method, without having to not only use expensive equipment or a noble metal but also perform an additional process.

According to an aspect of the present invention, there is provided a method of manufacturing a palladium (Pd) thin film by using an electroless-plating method, the method including: manufacturing a reaction mixture by adding Pd salt and an alkaline pH regulator to an alcohol-water mixed solution; and forming a Pd thin film by putting a substrate in the reaction mixture and stirring the reaction mixture.

The alcohol-water mixed solution may be a mixed solution containing 70 to 90 wt % of alcohol and 30 to 10 wt % of water.

The alcohol may be C1 to C4 alcohol.

The Pd salt may be selected from the group consisting of Pd nitrate, Pd chloride, Pd iodide, and Pd (II) acetate.

The alkaline pH regulator may be selected from the group consisting of butylamine, ethylamine, propylamine, pentylamine, and triethylamine.

The substrate may be formed of a material selected from the group consisting of glass, plastic, and indium tin oxide (ITO).

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
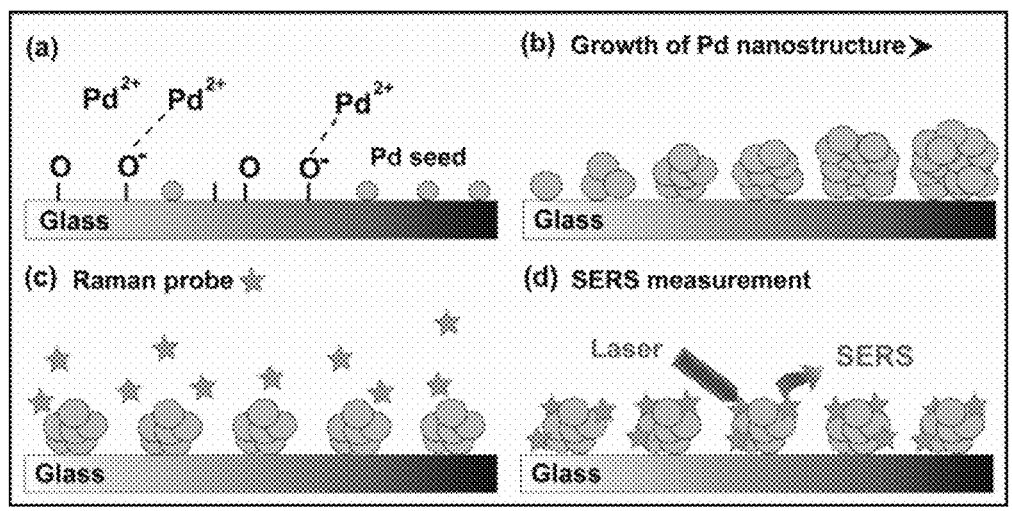
FIG. 1 is schematic diagrams for describing a process of manufacturing a palladium (Pd) thin film by using an electroless-plating method and a process of surface enhancement Raman scattering (SERS) activity.

Hereinafter, a method of manufacturing a palladium (Pd) thin film by using an electroless-plating method, according to one or more embodiments of the present invention, will now be described in detail.

First, a reaction mixture was manufactured by adding Pd salt and an alkaline pH regulator to an alcohol-water mixed solution.

Here, alcohol is a strong reducing agent.

After putting the substrate into the reaction mixture, the reaction mixture was stirred to form a Pd thin film.

The alcohol-water mixed solution was prepared such that the alcohol-water mixed solution contained 70 to 90 wt % of alcohol and 30 to 10 wt % of water.

The alcohol was C1 to C4 alcohol, and the Pd salt was selected from the group consisting of Pd nitrate, Pd chloride, Pd iodide, and Pd (II) acetate.

The alkaline pH regulator was selected from the group consisting of butylamine, ethylamine, propylamine, pentylamine, and triethylamine, and the substrate was formed of a material selected from the group consisting of glass, plastic, and indium tin oxide (ITO).

Although Pd is not currently widely used as much as platinum (Pt), Pd is an important transition metal having high catalytic activity. Such Pd has a large surface area with respect to a low price and volume, compared to Pt. In detail, due to a distinctive property of absorbing hydrogen ($H_2$), recent studies on Pd are focused on a nanostructure of Pd, and a hydrogen sensor, hydrogen storage device, and a catalysis using Pd.

Pd has intrinsically non- or very weak activity towards surface enhancement Raman scattering (SERS), and Pt, rhodium (Rh), ruthenium (Ru), iron (Fe), cobalt (Co), and nickel (Ni), which are transition metals, also show the same tendency.

Accordingly, it is difficult to check a catalytic reaction by detecting an SERS spectrum of an agent adsorbed onto a product and a surface manufactured based on Pd. Nevertheless, there have been continuous attempts to increase SERS activity by using the Pd nanoparticles.

According to an embodiment of the present invention, a SERS active Pd thin film is formed on a dielectric substrate formed of, for example, glass, via a simple one-step process. A particle size of Pd nanoparticles was conveniently adjusted by changing a molar ratio of the Pd salt and the alkaline pH regulator, and SERS spectra of benzenthiol (BT) and organic isonitrile were clearly identified even in a substrate on which a Pd thin film is formed, according to a nanostructure of aggregated Pd. An enhancement factor (EF) measured by using BT as a prototype molecule reached $1.8\times10^3$ using an excitation source of 514.5 nm.

Moreover, it was checked that 2,6-dimethylphenylisocyanide (2,6-DMPI) was adsorbed on-top and three-fold hollows sites of Pd nanostructures through an isocyanide group.

EXAMPLE 1

Manufacturing Pd Thin Film

First, palladium(II) nitrate dehydrate ($Pd(NO_3)_2 2H_2O$) having 99% purity, butylamine ($C_4H_9NH_2$) having 99.5 purity, BT having 99% purity, and 2,6-DMPI having 96% purity, which are manufactured by Aldrich, and used as received. Other materials were prepared in reagent levels, and anhydrous ethyl alcohol (absolute alcohol) having 99.9% purity was bought from J. T. Baker. Highly pure water filtered through a Milipore filter had resistivity higher than 18.0 MΩ·cm.

A reaction mixture was manufactured by mixing ethanol and water in a volume ratio of 8:2 to prepare a water-ethanol mixed solution, and then putting 10 ml of 10 mM Pd nitrate ($Pd(NO_3)_2$) and putting 40 μl of butylamine to the water-ethanol mixed solution.

Then, a 50 mm×10 mm×1 mm slide glasses bought from Marienfield as a substrate were soaked in a piranha solution for 30 minutes and sonicated in distilled water for 10 minutes. Next, the substrate was rinsed with ethanol and dried in an oven at 60° C. for 1 hour.

The washed substrate were dipped in the reaction mixture and incubated at 70±1° C. for 12 hours in a polyethylene container and were sufficiently stirred so as to deposit a Pd thin film on the substrate.

Then, the Pd-deposited substrate was washed with ethanol, and dried in the air.

EXAMPLE 2

Adjusting Molar Ratio of Pd Salt and Alkaline pH Regulator

In order to compare Pd particle sizes on the substrate according to a molar ratio of Pd nitrate to butylamine. A reaction mixture having Pd nitrate with 80, 100, and 140 μl of butylamine was prepared and slide glasses dipped in a reactions mixture so as to manufacture Pd thin films having different Pd particle sizes.

Molar ratios of Pd ions:butylamine were respectively 1:8, 1:10, and 1:40.

EXAMPLE 3

Preparing for SERS Measurement

In order to measure SERS spectra of BT and 2,6-DMPI, a Pd-deposited slide was put into an ethanolic solution containing 10 mM BT and 2,6-DMPI. Then, a solvent was evaporated and the Pd-deposited slide was washed with ethanol for 3 hours.

EXPERIMENT EXAMPLE 1

Analyzing Pd Thin Film

An ultraviolet-visible spectrum (UV-vis) was obtained by using a spectrometer (Avantes 3648). A scanning electron microscopic image (hereinafter, referred to as an FE-SEM image) was obtained by using a field-emission scanning electron microscope (JSM-6700F), and at this time, the FE-SEM was operated at 2.0 kV. Energy dispersive X-ray (EDX, SUPRA 55VP) was used, and an X-ray diffractor (XRD) using Cu $K_\alpha$ radiation was conducted on Rigaku Model MiniFlex powder diffractometer. An X-ray photoelectron spectroscopy (XPS, AXISH) using Mg $K_\alpha$ X-ray was used As a light source.

Raman spectra were obtained by using a spectroscope including an integral microscope (Olympus BH2-UMA), such as Renishaw Raman system Model 2000. 514.5 nm line from a 20 mW argon ion ($Ar^+$) laser (Melles-Griot Model 351MA520) was used as an excitation source. A Raman band of a silicon wafer at 520 $cm^{-1}$ was used to calibrate the spectrometer. Accuracy of the spectral measurement was estimated to be better than 1 $cm^{-1}$.

Atomic force microscopy images were obtained by using a Digital Instruments Nanoscope IIIa system, and at this time, using an 125 μm long etched silicon cantilever with nominal spring constant of 20 to 100 N/m (Nanoprobe, Digital Instruments). Topographic images were recorded in a tapping mode with a driving frequency of 300 at a scan rate of 2 Hz.

<Result 1> Forming Pd Thin Film on Substrate

FIG. 1 is schematic diagrams for describing a process of manufacturing a Pd thin film by using an electroless-plating method and a usage to detect chemicals by SERS activity.

In FIG. 1 (a), a glass substrate that is negatively charged is shown based on properties, and since the hydroxyl groups of a glass surface are partially deprotonated in water-ethanol mixed solution, Pd ions ($Pd^{2+}$) were particularly effectively arranged.

As Pd ions ($Pd^{2+}$) were added, oxygen sites combined to Pd consequently operated as a seed for growing Pd nanostructures on the substrate. Here, forming a Pd thin film on the substrate means that a pure ethanolic aqueous solution containing Pd nitrate ($Pd(NO_3)_2$) and butylamine forms a colloidal Pd nanostructure.

In order to form the Pd thin film on the glass substrate, an amount of water in the high purity ethanol aqueous solution was adjusted. If the amount of water was not adjusted, Pd nanostructures did not form on the substrate. Reducing power of the pure ethanolic aqueous solution containing butylamine was sufficient to form the Pd nanostructures even in the solution state. A bulk reaction did not start and Pd nanostructures start to form on the substrate when water was added to the pure ethanolic aqueous solution. On the other hand, when concentration of water increased, not only forming of Pd nanoparticles was blocked, but also developing of the Pd nanostructures on the glass substrate was blocked. Accordingly, in order to adjust reducing power of the water-ethanol mixed solution, a volume ratio of ethanol:water was adjusted to be 8:2.

When the Pd nanostructure started to form as shown in FIG. 1 (b), an analyte solution adsorbed onto the substrate where the Pd thin film is formed, as shown in FIG. 1 (c). Chemisortion or physisortion of analyte molecules may be detected via SERS as shown in FIG. 1 (d).

Figure 2:
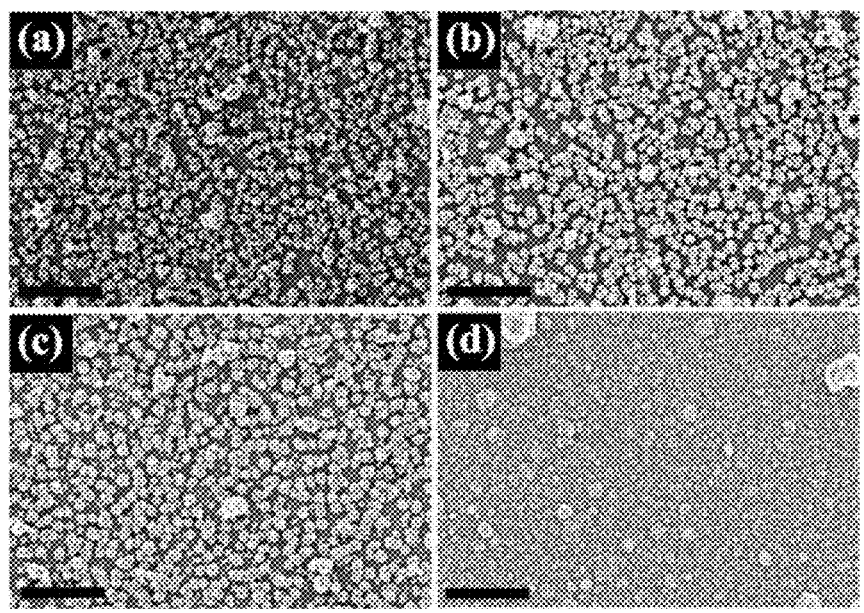
FIG. 2 is field emission scanning electron microscopic (FE-SEM) images of a Pd thin film manufactured by adjusting a molar ratio of Pd nitrate:butylamine from 1:4 to 1:40.

<Result 2> Changing Properties of Pd Thin Film According to Molar Ratio of Pd Nitrate:Butylamine FIG. 2 is FE-SEM images of a Pd thin film manufactured by adjusting a molar ratio of Pd nitrate:butylamine from 1:4 to 1:40. Here, a size of a scale bar is 1 μm.

Referring to FIG. 2, it is determined that a Pd thin film is formed on a substrate. An mean grain size was 85±10 nm when the molar ratio of Pd nitrate:butylamine was 1:4, 133±22 nm when the molar ratio was 1:8, and 165±23 nm when the molar ratio was 1:10. When butylamine was excessively used to form the Pd thin film, the glass substrate was completely covered by Pd nanostructures as shown in FIG. 2 (d). Accordingly, when the molar ratio was 1:40, Pd particles were not determined explicitly. In other words, when the molar ratio of butylamine increases, larger and more aggregated Pd grains are generated.

Figure 3:
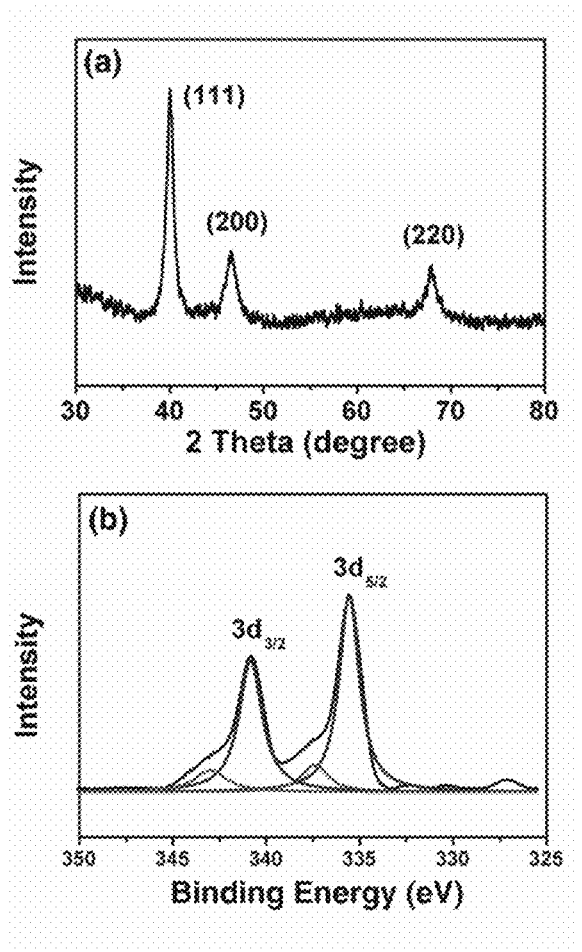
FIG. 3 illustrates X-ray diffraction (XRD) and X-ray photoelectron spectroscopy (XPS) graphs of a Pd thin film manufactured when a molar ratio of Pd nitrate:butylamine is 1:10.

FIG. 3 illustrates X-ray diffraction (XRD) and X-ray photoelectron spectroscopy (XPS) graphs of a Pd thin film manufactured when a molar ratio of Pd nitrate:butylamine is 1:10.

Referring to FIG. 3 (a), XRD peaks were shown at 40.1°, 46.6°, and 68.0° corresponding to reflections of (111), (200) and (220) a crystalline plane of a Pd cube respectively. A crystalline size of Pd nanostuctures was calculated via a Scherrer equation by using a half width of intense reflection about 12 nm. Referring to the FE-SEM image of FIG. 2 (c), the latter was 14 times smaller than a apparent size determined from the FE-SEM image. Such discrepancy may be because the grains of a Pd thin film actually have diameters smaller than or equal to 12 nm.

Referring to FIG. 3 (b), looking at an XPS of a Pd thin film manufactured when a molar ratio of Pd nitrate:butylamine was 1:10, two strong peaks were shown when binding energy (BE) was 335.7 eV and 340.8 eV. The two strong peaks are attributed to arise from $Pd_{3d5/2}$ and $Pd_{3d3/2}$ of a $Pd_0$ metal. Actually, the two strong peaks are asymmetrical in shape with shoulders at higher BE values, 337.4 eV and 342.9 eV corresponding to $Pd_{3d5/2}$ and $Pd_{3d3/2}$. Although an original shoulder peak is not clear, the peaks are originated from the $Pd^{2+}$ species, assignable to PdO, which often accompanies $Pd^0$ left in the oxygen-containing environment.

<Result 3> Checking SERS Activity of Manufactured Pd Thin Film

Considering that an SERS effect is generally activated in aggregated structures of metal particles in the range of 20 to 200 nm, it was predicted that the substrate on which the Pd thin film is formed may be active with respect to SERS. Before measuring activity of SERS, optical properties of the Pd thin film were first examined.

Figure 4:
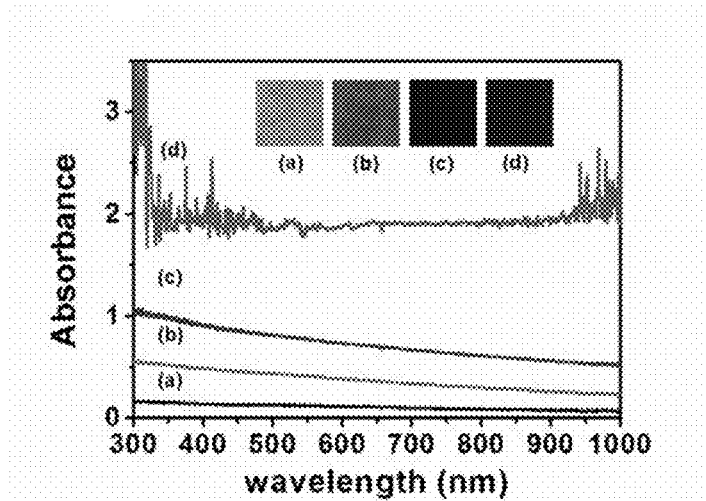
FIG. 4 is a graph showing an ultraviolet-visible spectrum of a Pd substrate.

FIG. 4 is a graph showing an UV-vis spectrum of a Pd substrate. Here, UV-vis spectra of 4 substrates on which a Pd thin film is formed are shown. A distinctive peak was not found within a wavelength range from 300 nm to 1000 nm, and only a gradual increase in absorption can be identified.

Figure 5:
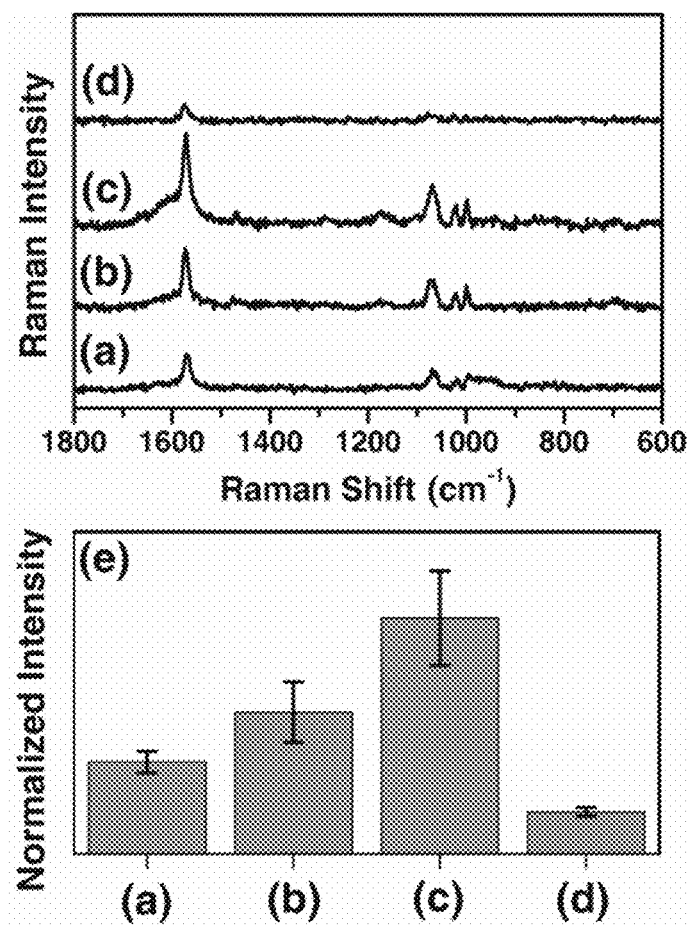
FIG. 5 illustrates a graph of a general SERS spectrum of a Pd thin film to which benzenthiol (BT) is adsorbed and a graph showing intensity of a relative Raman peak of BT at 1574 $cm^{-1}$.

Activity of an SERS effect of the substrates on which the Pd thin film is formed was measured by using BT as a model compound. FIG. 5 illustrates a graph of a typical SERS spectrum of a Pd thin film to which BT is adsorbed. FIG. 5 (a) illustrates a molar ratio of Pd nitrate:butylamine 1:4, FIG. 5 (b) illustrates a molar ratio of Pd nitrate:butylamine 1:8, FIG. 5 (c) illustrates a molar ratio of Pd nitrate:butylamine 1:10, and FIG. 5 (d) illustrates a molar ratio of Pd nitrate:butylamine 1:40. Referring to FIG. 5, a peak of SERS was very strong when a molar ratio of Pd ion:butylamine was 1:10 and other peaks of SERS were weak. Here, the least enhancement was shown when the molar ratio of Pd ion:butylamine was 1:40 according to relatively flat morphology. This shows that the importance of the gap or crevices among the metal nanostructures while measuring an SERS effect.

An enhancement factor (ER) of an SERS effect may be calculated as follows.

$$EF=(I_{SERS}/I_{NR})(N_{NR}/N_{SERS})$$ [Equation 1]

Here, $I_{SERS}$ and $I_{NR}$ respectively denote SERS intensity of a thin film when a molar ratio of Pd ion:butylamine is 1:10 and intensity of normal Raman (NR) scattering intensity when BT is bulk. $N_{SERS}$ and $N_{NR}$ are the number of BT molecules illuminated by the laser light to obtain the corresponding SERS and NR spectra, respectively. $I_{SERS}$ and $I_{NR}$ are values measured at 1574 $cm^{-1}$, and $N_{NR}$ and $N_{SERS}$ are calculated based on the basis of the estimated concentration of surface BT species, density of bulk BT and the sampling areas. It was assumed that the equilibrated surface concentration of BT is same as that on Au and Ag are 7.1×$10^{-10}$ mol/$cm^2$. Referring to FIG. 3, Taking the sampling area as well as the surface roughness factor obtained from the AFM measurement of a Pd thin film in which a molar ratio of Pd ion:butylamine was 1:10 into account, $N_{SERS}$ was calculated to be 1.2×$10^{-17}$ mol. When taking the NR spectrum of pure BT, the sampling volume will be the product of the laser spot and the penetration depth (~15 μm) of the focused beam. As the density of BT is 1.07 g/$cm^3$, $N_{NR}$ is calculated to be 1.1×$10^{13}$ mol. Since the intensity ratio, $I_{SERS}/I_{NR}$, is measured up to be 0.2 for a Pd thin film in which a molar ratio of Pd ion:butylamine was 1:10 at 514.5 nm excitation, EF can then be as large as $1.8 \times 10^3$. As shown in FIG. 5, five different spots were randomly selected to take the SERS spectra, the peak intensities at 1574 cm$^{-1}$ were also normalized with respect to that of a silicon wafer used in the instrument calibration. The fact that the relative standard deviation was less than 10% for all Pf films clearly illustrates the homogenous characteristics of Pd thin films.

<Result 4> Evaluating SERS Activity of Manufactured Pd Thin Film

Figure 6:
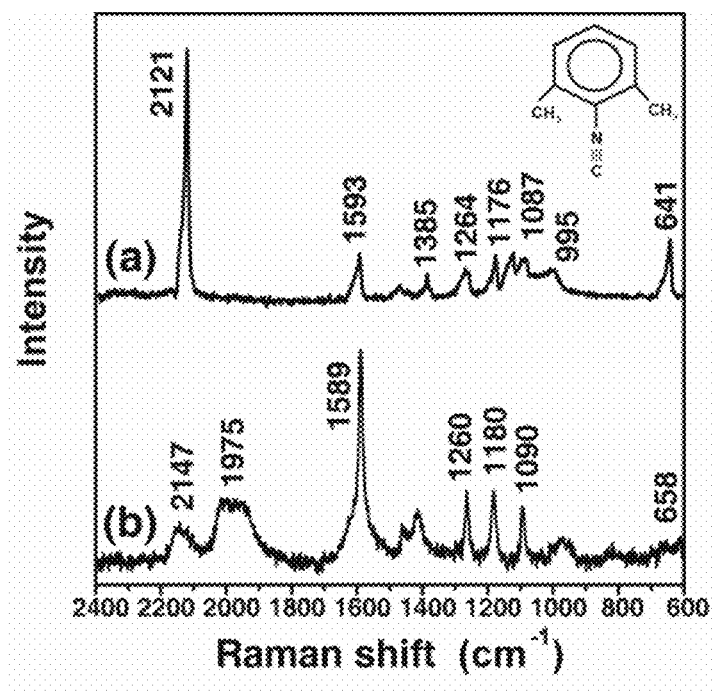
FIG. 6 is a graph of a normal Raman scattering (NR) spectrum of 2,6-dimethylphenylisocyanide (2,6-DMPI) in a solid state and a graph of an SERS spectrum of 2,6-DMPI absorbed to a Pd thin film.

Here, since an NC stretching frequency is very sensitive with respect to an adsorbed metal containing Au, Ag, and Pt, it was checked that organic isonitrile satisfactorily adsorbed fairly well onto such a type of metal. An SERS spectrum of 2,6-DMPI was measured to evaluate SERS activity of a Pd thin film, and FIG. 6 illustrates a spectrum obtained from a Pd thin film in which a molar ratio of Pd ion:butylamine was 1:10. FIG. 6 (b) illustrates that the SERS spectra of 2,6-DMPI and the spectrum obtained from a Pd thin film, FIG. 6(a) shows the NR spectrum of 2,6-DMPI measured based on an in neat solid state for reference. the NC stretching and the C—NC stretching bands appear at 2121 and 641 cm$^{-1}$, respectively, while the ring CC stretching and the in-plane ring breathing bands appear at 1593 and 995 cm$^{-1}$, respectively. In the SERS spectrum, the NC stretching and the C—NC stretching bands are observed at 2147 (1975) and 653 cm$^{-1}$, respectively. The ring CC stretching band is observed at 1589 cm$^{-1}$. Hence, the NC stretching band at 2147 cm$^{-1}$ has blue-shifted by as much as 26 cm$^{-1}$ upon the surface adsorption on Pd, although the ring band was red-shifted by 4 cm$^{-1}$. All of these are due to the adsorption of 2,6-DMPI on Pd via the -NC group. In particular, the substantial blue-shift is associated with the antibonding character of the carbon lone pair electrons of the NC group. The donation of these electrons to Pd should increase the strength of the NC bond. Furthermore, there is another peak, even stronger, at 1975 cm$^{-1}$ in FIG. 6(b). In an earlier investigation of SERS spectrum of 2,6-DMPI on laser-ablated Pt nanoaggregates, three bands appeared at 2166, 2124, and 1997 cm$^{-1}$ in the NC stretching region, and these three bands were attributed to the adsorption of 2,6-DMPI on the on-top, 2-fold bridge, and 3-fold hollow sites, respectively, of Pt nanoaggregates. It is therefore tempting to assign the 2147 and 1975 cm$^{-1}$ bands in FIG. 6(b) to the NC stretching modes of 2,6-DMPI adsorbed on the on-top and the 3-fold hollow sites of Pd nanostructures on glass substrates, respectively.

Aryl isocyanide can be a good π acceptor. Thus, it may not be unusual to observe multiple NC stretching peaks due to the π back-donation from Pd. The NC stretching frequencies observable from 2,6-DMPI on Pd are even about 19 to 22 cm$^{-1}$ lower than their counterparts on Pt, suggesting that the π back-donation capability of Pd must be greater than that of Pt.[37]

According to the method of manufacturing a Pd thin film by using an electroless-plating method of one or more embodiments of the present invention, a Pd thin film having an SERS effect may be easily manufactured without having to use expensive additional equipment, such as a vacuum device.

In detail, according to the method, electroless-plating may be performed even on an insulating substrate formed of, for example, glass, and a size of a Pd thin film formed on a substrate may be adjusted, and thus the substrate may be applied to various electrochemical products.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of manufacturing a palladium (Pd) thin film by using an electroless-plating method, the method comprising:
   manufacturing a reaction mixture by adding Pd nitrate as Pd salt and butylamine as an alkaline pH regulator in a molar ratio of 1:10 to an alcohol-water mixed solution, wherein the alcohol-water mixed solution is a mixed solution containing 80 wt % of ethanol and 20 wt % of water, and the substrate is formed of a glass; and
   forming a Pd thin film by putting a substrate in the reaction mixture and stirring the reaction mixture.

2. A method of manufacturing a palladium (Pd) thin film having a surface enhancement Raman scattering (SERS) activity by using an electroless-plating method, the method comprising:
   manufacturing a reaction mixture by adding Pd nitrate as Pd salt and butylamine as an alkaline pH regulator in a molar ratio of 1:10 to an alcohol-water mixed solution, wherein the alcohol-water mixed solution is a mixed solution containing 80 wt % of ethanol and 20 wt % of water, and the substrate is formed of a glass; and
   forming a Pd thin film by putting a substrate in the reaction mixture and stirring the reaction mixture,
   wherein the Pd thin film has the surface enhancement Raman scattering (SERS) activity when the molar ratio of the Pd salt and the alkaline pH regulator is 1:10.

* * * * *